(12) United States Patent
Chinkov et al.

(10) Patent No.: US 8,115,032 B2
(45) Date of Patent: Feb. 14, 2012

(54) PROCESS FOR THE SYNTHESIS OF A PROPARGYLIC ALCOHOL

(75) Inventors: Nicka Chinkov, Haifa (IL); Aleksander Warm, Arbaz (CH); Erick Carreira, Zürich (CH)

(73) Assignee: Lonza Ltd., Basel (CH)

( * ) Notice: Subject to any disclaimer, the term of this patent is extended or adjusted under 35 U.S.C. 154(b) by 0 days.

(21) Appl. No.: 12/741,247

(22) Filed: Mar. 28, 2011

(65) Prior Publication Data

US 2011/0172464 A1  Jul. 14, 2011

Related U.S. Application Data

(63) Continuation of application No. 61/167,908, filed on Apr. 9, 2009.

(30) Foreign Application Priority Data

Apr. 9, 2009 (EP) .................................. 09005215

(51) Int. Cl.
*C07C 211/00* (2006.01)
*C07C 215/00* (2006.01)
(52) U.S. Cl. ........................................ 564/442; 564/443
(58) Field of Classification Search .................. None
See application file for complete search history.

(56) References Cited

U.S. PATENT DOCUMENTS

| 6,015,926 A * | 1/2000 | Chen et al. ...................... 564/442 |
| 2006/0217552 A1* | 9/2006 | Jiang et al. ..................... 544/286 |

FOREIGN PATENT DOCUMENTS

| WO | 9520389 | 8/1995 |
| WO | 9637457 | 11/1996 |
| WO | 9830540 | 7/1998 |
| WO | 9830543 | 7/1998 |
| WO | 9851676 | 11/1998 |
| WO | 2004087628 | 10/2004 |

OTHER PUBLICATIONS

Jiang et al., "Zn(II)-Mediated Alkynylation-Cyclization of o-Trifluoroacetyl Anilines: One-Pot Synthesis of 4-Trifluoromethyl-Substituted Quinoline Derivatives", J. Org. Chem, vol. 67, pp. 9449-9451; 2002.

Jiang et al., "Alkynylation of Carbonyl Compounds with Terminal Acetylenes Promoted by ZnCl2 and Et3N: Simple, Mild and Efficient Preparation of Propargylic Alcohols", Tetrahedron Letters, vol. 43, pp. 8323-8325; 2002.

* cited by examiner

*Primary Examiner* — Karl J Puttlitz
(74) *Attorney, Agent, or Firm* — Hoffman & Baron, LLP

(57) ABSTRACT

A process for the preparation of the compound of formula

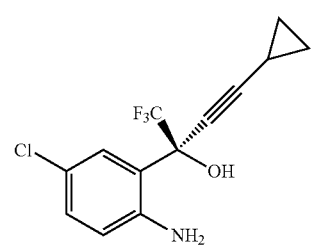

I

12 Claims, No Drawings

PROCESS FOR THE SYNTHESIS OF A PROPARGYLIC ALCOHOL

This application is the U.S. National Phase of, and Applicants claim priority from, International Application Number PCT/EP2010/002225 filed Apr. 9, 2010, U.S. Provisional Patent Application bearing Ser. No. 61/167,908 filed Apr. 9, 2009 and European Patent Application No. 09005215.0 filed on Apr. 9, 2009, which are incorporated herein by reference in their entirety.

BACKGROUND OF THE INVENTION

The invention is directed to a process for the preparation of the compound of formula,

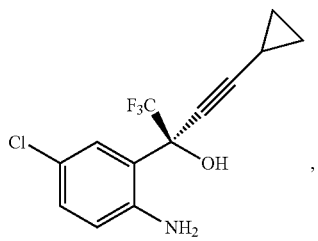

I i.e. 2-(2-amino-5-chlorophenyl)-1,1,1-trifluoro-4-cyclopropyl-but-3-yn-2-ol (SD573). This compound is an important intermediate for the preparation of (−)-6-chloro-4-(cyclopropyl-ethynyl)-4-trifluoromethyl-1,4-dihydro-2H-3,1-benzoxazin-2-one, which is a potent reverse transcriptase inhibitor for the treatment of HI viruses.

Jiang et al. disclosed in *Tetrahedron Lett.* 2002, 43, 8323-8325 and *J. Org. Chem.* 2002, 67, 9449-9451 the reaction of acetylene derivatives with aldehydes and ketones in the presence of equimolar amounts of a zinc(II) compound to give several racemic propargylic alcohols. Chiral compounds are not mentioned at all.

WO-A-95/20389, WO-A-96/37457, WO 98/30543 and WO 98/30540 disclose several processes for the production of chiral propargylic alcohols useful for the synthesis of pharmaceuticals. WO-A-98/51676 discloses a process wherein by addition of a first chiral and optionally a second additive in a zinc(II) mediated reaction the chiral product is obtained in high enantiomeric excess. The disadvantage of said process is the use of high amounts of expensive zinc catalysts and chiral compounds.

WO-A-2004/87628 further discloses facultative use of a chiral auxiliary in an equivalent molar amount in respect of the zinc(II) compound for the production of chiral propargylic alcohols mentioned above.

A main problem to be solved was therefore to supply an alternative process for the production of DMP266. A further problem was to reduce the amounts of catalyst and other components to be added during the reaction, in order to facilitate the workup procedures of the product and to promote industrial production.

DESCRIPTION OF THE INVENTION

The problem is solved by the process of claim 1. The inventive process comprises the addition of the product to the reaction mixture as a chiral mediator, which allows to reduce the amount of further chiral auxiliaries. Presence of the chiral product from the beginning of the reaction has the advantageous side effect that the amount of the zinc(II) catalyst can be reduced compared to processes known in the art. Furthermore, the addition of the compound of formula I allows to dispense with chiral auxiliaries, while still the chiral product is formed in high enantiomeric excess (ee).

Claimed is a process for the preparation of the compound of formula

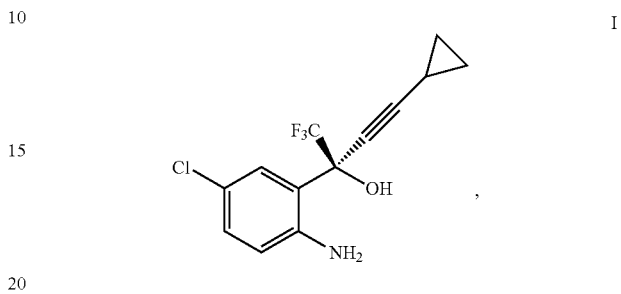

I said process comprising the steps of
(i) preparing a mixture of a zinc(II) catalyst, an initial amount of the compound of formula I in a molar ratio to the zinc(II) catalyst from 0.1:1 to 2:1, and optionally a chiral auxiliary in a molar ratio to the zinc(II) catalyst from 0.1:1 to 3:1, and
(ii) adding to said mixture
(a) the compound of formula

II (b) a base, and
(c) the compound of formula

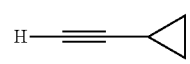

III at a mixing temperature from −78 to 30° C., and
(iii) heating the mixture obtained in step (ii) to 10 to 50° C. until completion of the reaction, to obtain the compound of formula I.

Regarding the addition of compounds in step (ii) the inventive process does not rely on a specific order of addition. In a preferred embodiment the compounds of formula II and the base are added simultaneously, either separately or as a mixture. The compound of formula II may also be added before or after the addition of compound formula III or both compounds may added simultaneously, either separately or as a mixture. In the latter case preferably the compound of formula II is fed together with the base.

The process is designed to obtain the compound of formula I with an enantiomeric excess (ee) of at least 60%, preferably with an ee of at least 70%, more preferred of at least 80%, and even more preferred of at least 90%.

In a preferred embodiment the reaction is carried out in the presence of a proton source selected from the group consisting of $C_{1-6}$-alcohols, phenols, benzyl alcohols, and linear or branched $C_{2-5}$-alkanoic acids, each of said $C_{1-6}$-alcohol, phenol and benzyl alcohol optionally being substituted with one or more halogen atoms, nitro, methyl or aryl groups, said $C_{2-5}$-alkanoic acid optionally being substituted with one or more halogen atoms. Both, the alcohol and the acid facilitate the proton exchange. Especially the addition of the acid is not intended to change the pH of the solution. The alcohol and the acid may be added at any time before completion of the reaction.

Preferably the zinc(II) catalyst is used in the process in a total molar ratio to the compound of formula II from 0.1:1 to 0.3:1. By using the product itself as the main chiral auxiliary the amount of the zinc(II) catalyst needed in the reaction can be reduced remarkably compared to processes known in the art. The compound of formula I mediates the catalytic process and although the zinc(II) catalyst and the compound of formula I form a zinc(II) complex with a certain stoichiometry it is not necessary to add the chiral compound of formula I and the zinc(II) catalyst in the same molar amount. Preferably the amount of the initially added compound of formula I is higher than the amount of the zinc(II) catalyst.

Suitable zinc(II) catalysts are for example di($C_{1-4}$-alkyl) zinc, diphenylzinc, $Zn(OTf)_2$ and $ZnCl_2$, wherein the alkyl moieties are independently selected from the group consisting of methyl, ethyl, propyl, isopropyl, butyl, isobutyl, sec-butyl and tent-butyl. OTf denotes a triflate (trifluoromethanesulfonate) group.

In a preferred embodiment the compound of formula I used as an auxiliary in step (i) is added in a molar ratio to the compound of formula III from 0.1:1 to 0.45:1. The compound of formula I and the zinc(II) catalyst are part of an chiral zinc(II) complex mediating an autocatalytic process. Autocatalysis in the present Zn(II) mediated autocatalytic process has the meaning that a chiral zinc(II) complex promotes the reaction in such a way, that the reaction may carried out in the absence of any further chiral auxiliary. Chiral compounds of formula I for use as initial amount may be obtained by production of racemic compounds and subsequent chiral resolution. Although said zinc(II) complex has a certain stoichiometry it is not necessary to add the chiral compound of formula I, or any optionally further auxiliary, and the Zn(II) catalyst in equimolar amounts.

In a preferred embodiment the compound of formula I used as a auxiliary in step (i) is added in a molar ratio to the compound of formula III from 0.1:1 to 0.45:1.

A chiral auxiliary may be used to increase the meditative effect of the compound of formula I to give the desired enantiomer of formula I. Preferably the auxiliary is selected from the group consisting of [R—(R,S)]-β-methyl-α-phenyl-1-pyrrolidineethanol ((1R,2S)-pyrrolidinylnorephedrine=(1R, 2S)-PNE), N-methylephedrine, ephedrine, N,N-dibenzoyle-phedrine, norephedrine, diethyl tartate, (1R,2R)-pseudoephedrine, cinchonine, (1S,2S)—N-methylpseudoephedrine, 2-(pyrrolidin-1-yl)ethanol, and N,N-dibutyl-2-amino-ethnol. (1R,2S)-PNE is a preferred auxiliary.

In a preferred embodiment in step (ii) the compound of formula II is used in a molar ratio to the compound of formula III from 0.8:1 to 3:1.

Addition of the compound of formula III can be carried out at a temperature from −78 to +30° C.

In a preferred embodiment the compounds of formula II are selected from the group consisting of p-methylbenzaldehyde, p-fluorobenzaldehyde, p-cyanobenzaldehyde, p-methoxybenzaldehyde, naphthalenealdehyde, cinnamaldehyde, $C_{3-20}$-alkane aldehydes, cycloheane carbaldehyde, cyclohexyl metyl ketone, methyl 4-metylcyclohexyl ketone, 1,1,1-trifluoroacetophenone and 2-(trifluoroaceto)-4-chloro-anilin.

In a further preferred embodiment of step (ii), the base is added in a molar ratio to the compound of formula III from 0.5:1 to 3:1.

Addition of the base can be carried out at a temperature from −40 to +10° C. In a preferred embodiment the compounds of formula III are selected from the group consisting of $C_{1-6}$-alkane acetylenes, cyclopropylacetylene, (1'-methyl)-cyclopropyl-acetylene and phenylacetylene.

A suitable base for the present process is a strong base such as sodium hydroxide, potassium hydroxide, caesium hydroxide, sodium hydride, potassium hydride, trimethylamine, triethylamine, potassium trimethylsilanolate, lithium trimethylsilanolate, lithium tert-butoxylate, lithium 2,2,2-trifluoroethoxylate, butyllithium and hexyllithium.

Preferably said base is an organometallic compound or a lithium organic salt.

In a preferred embodiment such organo lithium compound is selected from the group consisting of phenyllithium and ($C_{1-6}$-alkyl) lithium, such as methyllithium, ethyllithium, n-propyllithium, n-butyllithium (BuLi), n-hexyllithium (HexLi) or n-octyllithium.

In a further preferred embodiment the lithium organic salt is a lithium $C_{1-6}$-alkoxide.

Expediently, an organometallic lithium compound or lithium organic salt is used in the presence of a Lewis base or a nitrogen ligand such as diethyl ether, tetrahydrofuran (THF), tetramethylenediamine (TMEDA), N,N,N',N',N"-pentamethyldiethylenetriamine (PMDTA), or a sparteine such as (−)-sparteine, to deaggregate the lithium compound.

During the addition of the base the reaction mixture is preferably kept at a temperature from −40 to +10° C.

The inventive process may be carried out with or without solvent. In a preferred embodiment the process is carried out in an aprotic polar, a non-polar solvent or a mixture of aprotic polar and/or non-polar solvents.

The solvents of agents added in solution may be selected independently of each other. Particularly preferred the solvent is selected from the group consisting of Tetrahydrofuran (THF), benzene, chlorobenzene, o-, m-, p-dichlorobenzene, dichloromethane, toluene, hexanes, cyclohexane, pentane, 1,4-dioxane, cyclohexane, diethyl ether, tert-butyl methyl ether, diisopropyl ether, N-methylpyrrolidine, or a mixture thereof.

Here and hereinbelow the term "alkyl" represents a linear or branched alkyl group. By using the form "$C_{1-n}$-alkyl" the alkyl group is meant having 1 to n carbon atoms. $C_{1-8}$-alkyl represents for example methyl, ethyl, propyl, isopropyl, butyl, isobutyl, sec-butyl, tert-butyl, as well as linear and branched pentyl, hexyl, heptyl and octyl.

Here and hereinbelow the term "alkoxy" represents a linear or branched alkoxy group. By using the form "$C_{1-n}$-alkoxy" the alkyl group is meant having 1 to n carbon atoms. $C_{1-6}$-alkoxy represents for example methoxy, ethoxy, propoxy, isopropoxy, butoxy, isobutoxy, sec-butoxy, tent-butoxy, as well as linear and branched pentyloxy and hexyloxy.

Here and hereinbelow the term "aryl" represents an aromatic group, preferably phenyl or naphthyl.

If a $C_{1-6}$-alcohol is added as a proton source said $C_{1-6}$-alcohol is selected from the group consisting of methanol, ethanol, propanol, isopropyl alcohol, butanol, isobanol, sec-butanol, tent-butanol, pentanol, $(CH_3)_3CCH_2OH$, $(CH_3)_3CCH(CH_3)OH$, $Cl_3CCH_2OH$, $CF_3CH_2OH$, $CH_2=CHCH_2OH$, $(CH_3)_2NCH_2CH_2OH$. Examples for suitable benzyl alcohols and phenols are phenol, $PhCH_2OH$, $Ph_3COH$, 4-Cl-phenol and 4-$NO_2$-phenol.

In a further preferred embodiment a $C_{2-5}$-alkanoic acid added as a proton source is selected from the group consisting of acetic acid, proponic acid, butyric acid, $CF_3CO_2H$, $CH_3CHClCOOH$ and $(CH_3)_3CCO_2H$.

EXAMPLES

For calculation of the yield of the product, as well as for the calculation of the enantiomeric excess the product added in step (i) of the process is subtracted.

Example 1

Procedure for the autocatalytic formation of (S)-5-chloro-α-(cyclopropylethynyl)-2-amino-α-(trifluoromethyl)benzenemethanol (SD573 or (S)-2): A reaction flask, equipped with thermometer, mechanical stirrer, $N_2$ outlet and 2 dropping funnels, is dried and flushed with nitrogen. The flask is charged with (1R,2S)—N-pyrrolidinylnorephedrine ((1S, 2R)-PNE, 17.2% in THF/toluene at approx. 90:10 (w/w), 0.3 eq, 75 mmol) and the compound of formula I (SD573, 0.18 eq, 45 mmol). A solution of diethyl zinc(II) (DEZ, 0.24 eq, 1.1 M in toluene, 60 mmol) is dropwise added to the mixture of [R—(R,S)]-β-methyl-α-phenyl-1-pyrrolidineethanol ((1R, 2S)-PNE) and SD573 at 17° C., followed by 30 min of stirring at r.t. Cyclopropylacetylene (2 eq, 70.4% in toluene, 500 mmol) is added dropwise at a reaction temperature 15° C. and the mixture is stirred for additional 1.5 h at r.t. 2-Trifluoromethylcarbonyl-4-chloroaniline (SD570, a ketoaniline of formula II) (40.4% in THF/toluene, 1 eq, 250 mmol) is added simultaneously with hexyllithium (HexLi, 0.9 eq, 2.3 M in hexane, 225 mmol) at 0° C. to 1.8° C. within 7 h, by means of the two dropping funnels. The rate of the addition is kept as equal as possible for both reagents. At the completion of SD570 and base addition, 3 mL of anhydrous THF are added to wash down the leftovers of SD570 which crystallized on the edge of the funnel outlet. The reaction mixture is stirred at r.t. for 2 h, followed by heating to 40° C. A first aliquot was withdrawn after 2 h of heating and a second aliquot was withdrawn after 12 hours of heating. 0.5 mL of each aliquot is quenched with citric acid to pH=4 to 5, diluted by EtOAc, the organic phase is dried over $MgSO_4$, filtrated and submitted to the HPLC analysis (Hex/iPrOH=85:15 (w/w), chiralpack, AD-H, 25×4.6, flow=1 mL/min). The reaction affords the compound of formula I (SD573). 2 h aliquot: Enantiomeric excess (ee)=97.16%, conversion (Con.)=98.04%, selectivity (Sel.)=97%. 12 h aliquot: ee=97.03%, Con.=99.05%, Sel.=97.45%. Unless otherwise indicated the ee values in all examples have been corrected regarding the initial amount of the compound of formula I.

Example 2

Reaction according to example 1 but using only one equivalent (1.0 eq.) of Cyclopropyl-acetylene compared to the compound of formula II afforded the compound of formula I after 5 h reaction time at 40° C.: ee=89.3%, Con.=90%, Sel.=70.8%.

Example 3

Reaction according to example 1 but using racemic PNE as auxiliary afforded the compound of formula I after different reaction times at 40° C.: after 3 h: ee=64.6%, Con.=79.4%, Sel.=81.4%; after 4 h: Con.=80.6%, Sel.=87.1%; after 22 h: ee=68%, Con.=96%, Sel.=76.6%.

Example 4

Reaction according to example 1 but using 2-(N,N-dibutyl)-amino ethanol (DBAE) as auxiliary and maintaining the reaction mixture 12 h at r.t. after addition of the base before heating to 40° C., afforded the compound of formula I after different reaction times at 40° C.: 3 h aliquot: ee=64%, C=90.6%, S=71.4%; 5 h aliquot: ee=60%, C=85.6%, S=70.3%.

Example 5

Reaction according to example 4 but maintaining the reaction mixture 8 h at r.t. after addition of the base before heating to 30° C., afforded the compound of formula I: 0 h aliquot (before heating): ee=78%, Con.=35.2%, Sel.=84%; and at different reaction times at 30° C.: 2 h aliquot: ee=65.3%, Con.=80%, Sel.=54.4%; 22 h: ee=56.6%, Con.=94.6%, Sel.=61.2%.

The invention claimed is:
1. A process for the preparation of a chiral compound of formula

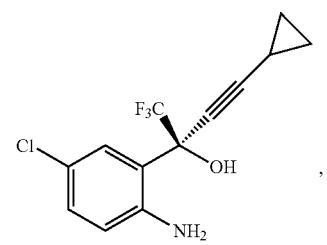

said process comprising the steps of
(i) preparing a mixture of a zinc(II) catalyst, a starting amount of the compound of formula I in a molar ratio to the zinc(II) catalyst from 0.1:1 to 2:1, and optionally a chiral auxiliary in a molar ratio to the zinc(II) catalyst of 0.1:1 to 3:1, and
(ii) adding to said mixture
(a) the compound of formula

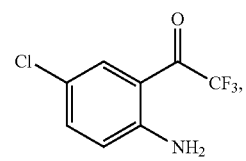

(b) a base
(c) the compound of formula

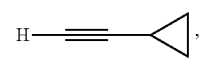

at a mixing temperature from −78 to 30° C., and
(iii) heating the mixture obtained in step (ii) to 10 to 50° C. until completion of the reaction.

2. The process of claim 1, wherein the process is carried out in the presence of a proton source selected from the group consisting of $C_{1-6}$-alcohols, benzyl alcohols, phenols and linear or branched $C_{2-5}$-alkanoic acids, each of said $C_{1-6}$-alcohol, phenol and benzyl alcohol optionally being substituted with one or more substituent selected from the group consisting of halogen atoms, nitro, methyl and aryl groups, said $C_{2-5}$-alkanoic acid optionally being substituted with one or more substituent selected from the group consisting of halogen atoms.

3. The process of claim 1, wherein the zinc(II) catalyst is used in a total molar ratio to the compound of formula II from 0.1:1 to 0.3:1.

4. The process of claim 1, wherein the zinc(II) catalyst is selected from the group consisting of di($C_{1-4}$-alkyl)zinc, diphenylzinc, Zn(OTf)$_2$ and ZnCl$_2$, wherein the alkyl moieties are independently selected from the group consisting of methyl, ethyl, propyl, isopropyl, butyl, isobutyl, sec-butyl and tert-butyl.

5. The process of claim 1, wherein in step (i) the product of formula I is added in a molar ratio to the compound of formula III from 0.1:1 to 0.45:1.

6. The process of claim 1, wherein in step (ii) the compound of formula II is used in a molar ratio to the compound of formula III from 0.8:1 to 3:1.

7. The process of claim 1, wherein the base is added in a molar ratio to the compound of formula III from 0.5:1 to 3:1.

8. The process of claim 1, wherein the base is an organometallic compound or a lithium organic salt.

9. The process of claim 8, wherein the organometallic compound is selected from the group consisting of phenyllithium or ($C_{1-8}$-alkyl) lithium.

10. The process of claim 8, wherein the lithium organic salt is a lithium $C_{1-6}$-alkoxide.

11. The process of claim 1, wherein the temperature during the addition of the base is of from −40 to +10° C.

12. The process of claim 1, wherein the reaction is carried out in an aprotic polar or non-polar solvent or a mixture of aprotic polar and/or non-polar solvents.

* * * * *